(12) United States Patent
Bru-Magniez et al.

(10) Patent No.: US 6,440,461 B1
(45) Date of Patent: Aug. 27, 2002

(54) POLY(METHYLIDENE MALONATE) MICROSPHERES, PREPARATION METHOD AND PHARMACEUTICAL COMPOSITIONS CONTAINING THEM

(75) Inventors: Nicole Bru-Magniez; Elias Fattal; Catherine Le Visage, all of Paris; Patrick Couvreur, Villebon sur Yvette; Pascal Breton, Tigy, all of (FR)

(73) Assignee: Virsol, Paris (FR)

( * ) Notice: Subject to any disclaimer, the term of this patent is extended or adjusted under 35 U.S.C. 154(b) by 0 days.

(21) Appl. No.: 09/673,255

(22) PCT Filed: Apr. 28, 1999

(86) PCT No.: PCT/FR99/01005

§ 371 (c)(1),
(2), (4) Date: Dec. 19, 2000

(87) PCT Pub. No.: WO99/55309

PCT Pub. Date: Nov. 4, 1999

(30) Foreign Application Priority Data

Apr. 29, 1998 (FR) .......................... 98D005424

(51) Int. Cl.⁷ .................. A61K 9/14; A61K 9/50; A61K 47/30; A61K 47/32; A61K 47/00
(52) U.S. Cl. ................ 424/486; 424/501; 514/772.3; 514/772.6; 514/785
(58) Field of Search ............... 424/486, 9.52, 424/497, 501; 514/772.3, 772.6, 785

(56) References Cited

U.S. PATENT DOCUMENTS 6,106,807 A 8/2000 Albayrak et al.

FOREIGN PATENT DOCUMENTS

| EP | 0583955 | 2/1994 |
|---|---|---|
| FR | 2755136 | 4/1998 |

OTHER PUBLICATIONS

Lescure et al, "Preparation and characterization of Novel Poly(methylidene Malonate 2.1.2)–Made Nanoparticles", Pharmaceutical Research, vol. 11, No. 9, pp. 1270–1277 (Sep. 1994).*

"Preparation and Characterization of Novel Poly (Methylidene Malonate 2.1.2.) –Made Nanoparticles", Lescure et al, Pharmaceutical Research, vol. 11, No. 9, Sep. 1994, pp. 1270–1277.

* cited by examiner

Primary Examiner—Thurman K. Page
Assistant Examiner—Blessing Fubara
(74) Attorney, Agent, or Firm—Dennison, Schultz & Dougherty

(57) ABSTRACT

The invention concerns novel microspheres particularly useful in pharmaceutics as particulate vectors for carrying biologically active substances, in particular hydrophilic substances, for oral administration. The invention is characterised in that said microspheres consist of a support material continuous lattice wherein is optionally dispersed a substance, said support material containing at least 70 wt. % of a homopolymer consisting of recurrent units corresponding to general formula (I):

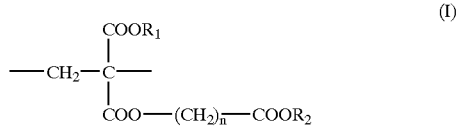

wherein: $R_1$ represents an alkyl group containing 1 to 6 carbon atoms or a $(CH_2)_m$—$COOR_3$ group wherein m is an integer ranging between 1 and 5 and $R_3$ represents an alkyl group having 1 to 6 carbon atoms; $R_2$ represents an alkyl group having 1 to 6 carbon atoms; and n is an integer ranging between 1 and 5. The invention is useful in pharmaceutics.

35 Claims, No Drawings

POLY(METHYLIDENE MALONATE) MICROSPHERES, PREPARATION METHOD AND PHARMACEUTICAL COMPOSITIONS CONTAINING THEM

BACKGROUND OF THE INVENTION

The object of the present invention is novel microspheres which are notably useful in the pharmaceutical field as particulate vectors intended for the transport of biologically active substances, in particular hydrophilic substances (peptides or proteins), with a view to an oral administration.

Another object of the invention is a method of preparing these microspheres, and pharmaceutical compositions containing them.

Within the context of the present description, the term "microspheres" is understood as signifying particles which are roughly spherical, of an average diameter of between 1 μm and 100 μm, preferably between 5 and 100 μm, and which are formed of a continuous matrix, which is more or less dense, of a support material.

These microspheres differ from the microcapsules which are constituted of a wall surrounding a cavity. It is, however, to be noted that the microspheres prepared in a multiple emulsion can comprise a collection of globules which are dispersed in the continuous network constituting them.

In this latter case, the total volume of these globules will generally represent a fraction of between 1:20 and 1:2 of the total volume of the microspheres.

Over the last years, many studies have enabled demonstrating that particulate systems based on polymers can be used for modifying the profile of release of a therapeutically active substance.

It is thus that the microspheres based on synthetic polymers, such as, for example, poly(lactic acid), poly(lactic acid-co-glycolic acid), polystyrene, poly(epsilon caprolactone), poly(methyl methacrylate), or based on methyl cellulose or ethyl cellulose have been prepared by various techniques.

However, the microspheres thus obtained are generally non-biodegradable, and when they are, they are characterised by a very delayed degradation with time.

Thus, in the case of microspheres based on poly(lactic) acid, for example, the degradation is not progressive and takes place at once after a significant time interval.

Further, the lactic polymers degrade in releasing products which are highly acidic which, not only lead to the autocatalysis of the degradation of the polymer, but are the origin of the induction of incompatibilities with the substances encapsulated.

In the case of the other polymers used, the microspheres have an extremely low speed of degradation, even have no degradation.

The staying time in the organism of such particles can limit the repeated application thereof in man.

Finally, the known microspheres are characterised for the most by a significant hydrophobicity which promotes strong interactions and often denaturing interactions with the substance to be encapsulated, in particular when the latter is of protein or peptide nature.

SUMMARY OF THE INVENTION

It has been discovered, and this constitutes the basis of the present invention, that it was possible to prepare novel microspheres which enable remedying the drawbacks of the microspheres of the state of the art.

Thus, according to a first aspect, the object of the present application is microspheres constituted of a continuous network of a support material in which a substance is optionally dispersed, characterised in that said support material contains at least 70% by weight of a homopolymer constituted of recurring units of the following general formula (I):

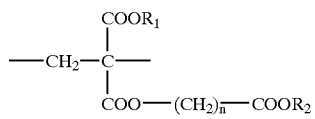

in which:

R$_1$ represents an alkyl group having 1 to 6 carbon atoms or a (CH$_2$)$_m$—COOR$_3$ group in which m is an integer of between 1 and 5 and R$_3$ represents an alkyl group having 1 to 6 carbon atoms;

R$_2$ represents an alkyl group having 1 to 6 carbon atoms; and n is an integer of between 1 and 5.

It has been demonstrated that on account of the chemical nature of the polymers forming their matrix, these novel microspheres:

have progressive and modulated degradation kinetics;

enable encapsulating, with great efficiency, hydrophilic substances, notably substances of biological origin.

Further, it has been observed, in an entirely surprising and unexpected manner, that these microspheres:

can induce a stimulation of the immune response when they are combined with an antigen;

enable in certain cases the suppression of hypersensitivity pathological reactions (induction of a tolerance) when they are administered via the oral route.

DETAILED DESCRIPTION OF THE INVENTION

Thus, it is the nature of the polymeric material forming the matrix of the microspheres which constitutes the originality of the present invention.

This polymeric material is essentially formed of a homopolymer constituted of recurring units of general formula (I).

Such polymers possess the remarkable property of being biocompatible and bioerodable, i.e. they can degrade chemically or biochemically by cleavage of the lateral substituents.

The speed of erosion of the microspheres in accordance with the invention being dependent upon the molecular weight of the support material, the speed can therefore by modulated simply by using a support material having a molecular weight adapted to the speed of erosion desired.

The microspheres according to the present invention thus possess a progressive and modulated bioerosion which enable, for example, the transport of a biologically active substance, dispersed in the support material, up to the location in the organism where its action will be the most efficient.

The bioerosion of the microspheres also prevents their accumulation in the organism; their use is therefore no more limited.

According to a particular characteristic, the homopolymer mentioned above is constituted of recurring units of the general formula (I) in which:

$R_1$ represents an alkyl group having 1 to 6 carbon atoms;

$R_2$ represents an alkyl group having 1 to 6 carbon atoms; and n is a number equal to 1;

and preferably in which $R_1$ and $R_2$ represent a $CH_2$—$CH_3$ group.

These different types of polymers of the poly (methylidene-malonate) family are particularly suitable for the encapsulation of hydrophilic substances, notably substances of biological origin, and optionally biologically active substances.

<<Biologically active molecule)) is understood as meaning, in a non-limiting manner, any molecule having a prophylactic or curative biological action, in vitro or in vivo, notably an anti-infectious agent, in particular an antiseptic, antibiotic, antiviral, antiparasitic or antimitotic agent, notably an anticancer agent.

Antibiotic or antiseptic agents which can be used can be rifampicin and colistine for example.

Didanosine, ribavirine, zidovudine, acyclovir, ganciclovir, foscarnet, vidarabine and zalcitabine can be cited in a non-limiting manner as examples of antiviral agents.

Cis-plastin and taxol can, for example, by used as anti-caner agents.

According to a currently preferred embodiment of the invention, the support material of the microspheres contains:

from 90% to 99.5% by weight of a homopolymer as defined above; and from 0.5% to 10% by weight of a copolymer comprising at least one sequence having a hydrophilic character and at least one sequence having a hydrophobic character, said sequence having hydrophobic character preferably comprising at least one recurring unit of the general formula (I).

Advantageously, the sequence having hydrophilic character of the copolymer mentioned above is selected from a poly(oxyethylene), a poly(vinyl alcohol), a poly(vinylpyrrolidone), a poly(N-2-hydroxypropyl methacrylamide), a poly(hydroxyethyl methacrylate), a hydrophilic poly(amino acid) such as a polylysine, a polysaccharide, and will preferably be a poly(oxyethylene).

The copolymer can have a block structure, preferably a di-block structure or tri-block structure, or a grafted structure.

The addition of such copolymers into the support material enables obtaining a homogeneous dispersion of the substance to be encapsulated inside each of the microspheres.

The addition also enables modulating the hydrophilic/hydrophobic ratio of the surface of the microspheres, and this enables preventing or limiting strong and often denaturing interactions with the substance to be encapsulated.

Further, these copolymers, the chemical nature of the hydrophobic sequence of which is identical to that of the homopolymer which essentially constitutes the microspheres, are particularly advantageous for the implementation of the currently preferred method of preparing the microspheres, as will be explained in more detail by the following.

In general, the microspheres in accordance with the present invention can be obtained by carrying out a method comprising:

preparing a multiple emulsion having three phases, the intermediate phase of which is constituted of a solution of polymer(s) constituting the support material in a volatile organic solvent, and evaporating said organic solvent, under conditions which enable causing the precipitation of the polymer around the droplets constituting the internal phase.

This multiple emulsion can be obtained in a classical manner by dispersing a first emulsion of the water-in-oil type in a second aqueous phase containing a stabilising agent.

This multiple emulsion can also be obtained by an "inverse" method which consists in pouring an aqueous solution into a first emulsion of the water-in-oil type. In an entirely unexpected way, this "inverse" method enabled obtaining results which are entirely remarkable, sometimes even better than those obtained by the classical technique mentioned above.

Thus, according to a second aspect, the present invention relates to a method of obtaining microspheres as described above, comprising:

a) preparing a first solution of the polymer(s) mentioned above constituting the support material in a volatile organic solvent optionally containing a surfactant agent, b) preparing a second solution non-miscible with the solution obtained in a), optionally containing said substance to be dispersed and optionally a surfactant agent, c) preparing a first emulsion by dispersing the second solution in the first solution, the continuous phase being constituted by the solution of polymer(s), d) preparing a second emulsion:

either by dispersing, with agitation, the first emulsion obtained in c) in a dispersing medium non-miscible with said first emulsion, said dispersing medium optionally containing a stabilising agent;

or by pouring with agitation; into said first emulsion, a solution constituted of a medium non-miscible with said first emulsion, said medium optionally containing a stabilising agent, e) evaporating said organic solvent with agitation.

According to a particular characteristic of the invention, the method mentioned above further comprises:

f) isolating the microspheres by centrifugation g) one or more successive washings of said microspheres h) lyophilising said microspheres.

The first step of the method of preparing the microspheres in accordance with the invention therefore comprises the preparation of an emulsion of the water-in-oil type preferably in the presence of a suitable surfactant agent, the oily or organic phase containing the polymer(s) intended to constitute the support material of said microspheres.

Firstly, a solution of the polymer(s) constituting the support material is prepared with the aid of a suitable volatile organic solvent optionally in the presence of a surfactant agent.

Advantageously, preformed polymers will be used in this step insofar as the homopolymers which essentially constitute the support material of the microspheres can be obtained under the conditions which enable a good characterisation in terms of molar mass and of mass dispersity.

The homopolymers which are constituted of recurring units of the general formula (I) can be prepared from monomers, for example by following the method described in the EP 283346 patent which corresponds to U.S. Pat. No. 4,931,584 and U.S. Pat. No. 5,142,098 patents which are incorporated herein by reference, said monomers being generally degassed under vacuum of a paddle pump to constant weight in order to remove the polymerisation inhibitor ($SO_2$).

These homopolymers will however be advantageously prepared anionically in an aprotic medium, for example by dispersion of the monomer in acetone, followed by the addition of sodium hydroxide under agitation, followed then by evaporating the acetone and drying the polymer thus obtained.

Other aprotic organic solvents such as acetonitrile, dioxan and tetrahydrofuran can be used instead of acetone.

The molecular mass of the homopolymer obtainable by carrying out this method can be perfectly mastered by a judicial choice of the conditions of implementation, and in particular of the concentration of the monomer in the organic phase, of the pH and of the molarity of the polymerisation initiator (sodium hydroxide).

In general, homopolymers having an average molar mass of 1,000 to 100,000, and preferably of 5,000 to 80,000, will be used within the context of the present invention.

The volatile organic solvent which can be used for the preparation of the first solution containing the polymer(s) constituting the support material will generally be selected such that its boiling point be lower than that of water. It will therefore be possible for this solvent to be removed easily during the final evaporation step by enabling the precipitation of the polymer.

Ethyl acetate constitutes a volatile organic solvent which is particularly suitable to this end.

The surfactants which can be used for stabilising the first emulsion can be of various natures and will be added to the organic phase containing the polymer(s) (first solution) and/or to the aqueous phase (second solution) which constitutes the dispersed phase.

It can be for example a poloxamer such as the product marketed under the designation Pluronic® F68, or even a poly(vinyl alcohol) such as the product marketed under the designation Mowiol® 40–88, or even a polysorbate, or a surfactant copolymer the hydrophobic sequence of which has a chemical nature which is identical to that of the homopolymer constituted of recurring units of the general formula (I).

It has been demonstrated that such surfactant copolymers and in particular poly(methylidene malonate) and polyoxyethylene copolymers are particularly advantageous insofar as they enable obtaining a very stable first emulsion on the one hand, and obtaining a good anchoring of the surfactant in the matrix after evaporation of the solvent on the other.

The surfactant copolymers mentioned above can be prepared by classical polymerisation techniques well known to the person skilled in the art.

Amongst these techniques, anionic polymerisation, radical polymerisation, or even the technique of coupling of the copolymer precursor sequences, will preferably be used, these sequences having been adequately functionalised beforehand at the end of the chain.

Anionic polymerisation is more particularly suitable for preparing block copolymers.

The anionic polymerisation comprises the sequential addition of the monomers and enables obtaining copolymers of a perfectly defined structure, the amounts of initiators and monomers engaged enables controlling the degree of polymerisation of each one of the sequences.

A block copolymer can also be obtained:
either by anionic polymerisation of a first monomer and reaction on the growing chain of a second monomer;
or by activation of a precursor polymer which will serve as initiator of the polymerisation of a second monomer.

The initiator agents which can be used within the context of these anionic polymerisations will generally be:

on the one hand, organometallic derivatives, such as butyllithium and particularly diphenylhexyllithium;
on the other, alkoxides and in particular macromolecular alkoxides such as a POE alkoxide which can be generated by activating a hydroxyl function with the aid of cumylpotassium, diphenyl methylpotassium, naphthalenepotassium.

The anionic polymerisation will generally be carried out in a solvent which is compatible with the various sequences of the copolymer.

In the case in which the sequence having hydrophilic character is constituted of a poly(oxyethylene) and the sequence having hydrophobic character is constituted of a poly(methylidene malonate), the block copolymers will be prepared preferably by successive anionic polymerisation of ethylene oxide and then of methylidene malonate or by activation of a commercial monohydroxylated polyoxyethylenated precursor and subsequent anionic polymerisation of the poly(methylidene malonate) sequence.

In general, tetrahydrofuran will preferably be used as polymerisation solvent, this product enabling working in a homogeneous medium and influencing the polymerisation kinetics favourably.

The monomers used for preparing the hydrophilic sequences will generally be commercial products.

The coupling technique is also more particularly suitable for preparing block copolymers.

This reaction is generally carried out from pre-synthesised and functionalised homopolymers, in the presence of a coupling agent and optionally in the presence of an activating agent, in a suitable solvent.

An α-carboxy group-functionalised poly(oxyethylene) homopolymer and an α-hydroxy group-functionalised poly(methylidene malonate) homopolymer will advantageously be used in the case of the preparation of the preferred copolymers according to the invention, the hydrophilic sequence of which is constituted of a poly(oxyethylene) and the hydrophobic sequence of which is constituted of a poly(methylidene malonate).

The α-carboxy group-functionalised poly(oxyethylene) homopolymer can be obtained for example by transforming a commercial α-hydroxy group-functionalised poly(oxyethylene) with succinic anhydride.

The α-hydroxy group-functionalised poly(methylidene malonate) homopolymer can be obtained directly by anionic synthesis in aqueous medium or by anionic synthesis in a solvent using an aqueous sodium hydroxide solution as polymerisation initiator.

Dicyclohexylcarbodiimide (DCCI) will advantageously be used as coupling agent which is particularly adapted to this polymerisation.

The coupling reaction can optionally be activated by basic catalysis, and will generally take place in a solvent which is compatible with the homopolymers, such as dichloromethane in particular in the particular case of the preferred copolymers of the invention.

The radical polymerisation is more particularly suitable for preparing grafted copolymers.

This polymerisation is generally carried out from a macromonomer, i.e. an oligomer which bears, on one of its ends, an ethylenic group which is radical polymerisable and which is able to react with a monomer to form a copolymer having a grafted structure.

This polymerisation will generally be carried out in the presence of an initiator in a suitable solvent.

It will be possible for various functionalised macromonomers to be used in the case of the preparation of the preferred copolymers, the hydrophilic sequence of which is constituted of a poly(oxyethylene).

It will be more particularly preferred to use a methacryloyl group-functionalised poly(oxyethylene) macromonomer.

Such a product can be commercial (Aldrich) and will be constituted for example by a poly(oxyethylene) chain of molar mass between 308 and 440 g/mol, or will be prepared from a commercial poly(ethylene glycol) monomethyl ether by coupling with methacrylic acid in dichloromethane to form a methoxy terminal function.

Such a macromonomer may even be prepared by activation of a poly(oxyethylene) and subsequent reaction with methacryloyl chloride.

It is also be possible for the copolymers having grafted structures to be prepared by transesterification of a poly (oxyethylene) monomethylether with the lateral ester chains of a pre-synthesised poly(methylidene malonate).

This transesterification will generally be carried out with alcohol in the presence of a catalyst at high temperature.

Copolymers the total molar mass of the sequences of which having hydrophobic character is between 1,000 and 80,000 g/mol, and preferably between 1,000 and 50,000 g/mol are particularly suitable within the context of the present invention.

Generally, it will be possible for the first emulsion serving for the preparation of the microspheres according to the invention to be obtained by means of a shearing homogeniser of the Ultraturrax type (13,500 rpm–5 minutes) for example.

The substance to be encapsulated is generally added to the dispersed aqueous phase of the first emulsion.

The second step of the method of preparing the microspheres in accordance with the invention comprises preparing a second emulsion:

- either by dispersing, with agitation, the first emulsion obtained in the first step in a dispersing medium non-miscible with said first emulsion, said dispersing medium optionally containing a stabilising agent;
- or by pouring with agitation into said first emulsion, a solution constituted of a medium non-miscible with said first emulsion, said medium optionally containing a stabilising agent.

Generally, the dispersing medium non-miscible with the first emulsion is an aqueous phase in which the first emulsion is introduced, preferably dropwise, and the emulsion is also prepared for example with the aid of a homogeniser of the Ultraturrax type (8,000 rpm; 5 minutes).

Poly(vinyl alcohol) constitutes a stabilising agent which is particularly suitable for the preparation of the second emulsion.

Optionally, this second step can be followed by a supplementary step of displacement of the organic solvent.

The third essential step of the method of preparing the microspheres in accordance with the invention consists in evaporating the volatile organic solvent having served for the preparation of the solution of the polymer(s).

In the particular case in which this solvent is ethyl acetate, this evaporation is carried out for a period of time of about 12 hours at ambient temperature, under magnetic agitation (1,400 rpm).

The person skilled in the art will select in an appropriate manner the various conditions of implementation of these three first essential steps of the method in accordance with the present invention as a function of the physico-chemical and morphological characteristics of the microspheres sought after.

Generally, these microspheres will have an average diameter of between 1 $\mu$m and 100 $\mu$m, preferably of between 5 $\mu$m and 50 $\mu$m for their application as vectors in the pharmaceutical field.

Generally, the microspheres obtained at the end of the third step will be isolated by centrifugation, washed, and optionally lyophilised.

According to a third aspect, the present invention also relates to pharmaceutical compositions containing the microspheres which have just been described. These compositions will generally be suitable for an administration via the oral route and will be presented for example in the form of tablets, gelatine capsules, powders or granules.

The present invention will now be illustrated by the following non-limiting Examples:

The following abbreviations are used in these Examples:

EO: ethylene oxide

POE: poly(oxyethylene)

MM 2.1.2: methylidene malonate of formula:

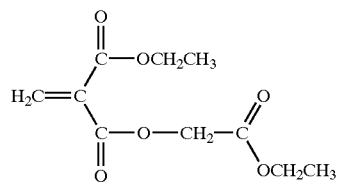

also designated as: 1-ethoxycarbonyl-1-ethoxycarbonyl methylene-oxycarbonylethene PMM 2.1.2: polymer constituted of recurring monomer units of formula:

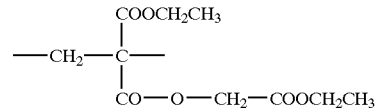

Furthermore, in these Examples:

the size of the microspheres was measured by the technique of the Coulter counter and the morphological examination carried out by sweeping electronic microscopy, either on the crude prepared microspheres, or after cryofracture;

the molecular mass of the polymers was determined by gel permeation chromatography (GPC).

EXAMPLE 1

100 mg of methylidene malonate 2.1.2 are dissolved in 10 ml of acetone with magnetic agitation. 100 microlitres of 0.1 N sodium hydroxide are added progressively with magnetic agitation. The polymerisation is maintained for 5 minutes and then 100 microlitres of 0.1 N HCl are added always with magnetic agitation. The acetone is all removed under vacuum. The polymer obtained is then washed with the aid of about 100 ml of distilled water and then dried under vacuum. The molecular mass of this polymer is 30,000.

280 mg of poly(methylidene malonate) are dissolved in 10 ml of ethyl acetate. 1 ml of aqueous phase containing 60 mg of ovalbumin is emulsified in the organic phase with agitation with the aid of an Ultraturrax at a speed of 13,500 rpm for 5 minutes. This emulsion is then added to 100 ml of a 2% aqueous solution of poly(vinyl alcohol), the agitation being made with the aid of an Ultraturrax at a speed of 8,000 rpm for 5 minutes. The evaporation of the ethyl acetate is carried out at ambient temperature overnight, with mechanical agitation (turning blade) at a speed of 1,400 rpm. The microspheres are collected after centrifugation at 4,000 rpm for 10 minutes and then washed 6 times with distilled water and each time they are subjected to a new centrifugation. After the last centrifugation, the microspheres are placed back in suspension in a volume of 3 ml of distilled water and are then lyophilised.

The microspheres thus obtained have an average diameter of 6 microns and 14.2% of the ovalbumin used in the preparation is encapsulated in the PMM 2.1.2 microspheres, and this corresponds to an encapsulation of 2.5% (w/w).

This preparation is administered via the oral route to C3H mice at the dose of 100 micrograms of encapsulated ovalbumin (per mouse per day) over 5 consecutive days. The last oral administration took place 7 days before the sensitisation of the animals to ovalbumin which is carried out by subcutaneous injection of free ovalbumin (100 micrograms per mouse) on days DO and D14. 90% of the mice survive the second injection while less than 30% of the mice administered with the microspheres without ovalbumin or with the same dose of non-encapsulated ovalbumin survive.

EXAMPLE 2

Carried out according to Example 1 but Pluronic F 68 is added into the aqueous phase containing the ovalbumin at a concentration of 2%.

EXAMPLE 3

Carried out according to Example 1 but 20 mg of POE-PMM copolymer are added into the aqueous phase containing the polymer.

In this example, a POE-PMM 2.1.2 block copolymer was used. This copolymer was obtained by successive polymerisation of the two monomers by starting with the preparation of the POE block, in carrying out the following experimental protocol.

The reactor (250 ml) in which the polymerisation is carried out is connected to a vacuum line enabling working under high vacuum and ridding of protic impurities.

The solvent (THF, 150 ml) purified of all traces of moisture is cryodistilled into the reactor at −70° C.

The initiator (potassium tert-butoxide (0.1N/THF); 10 ml) is then added with the aid of a syringe via a septum.

Ethylene oxide (5 g) is then introduced by cryodistillation.

The polymerisation is carried out at ambient temperature for 48 hours. After this time, a sample enables verifying, by gel permeation chromatography, the molar mass (4,000 g/mol) and the polymolecularity index (1.13) of the first sequence.

The MM 2.1.2 (0.5 ml), freshly degassed under vacuum to remove the $SO_2$ used as polymerisation inhibitor, is then added rapidly and at once at ambient temperature.

After 5 hours, the copolymer is deactivated by the addition of methanol and is precipitated in diethyl ether.

5 units derived from MM 2.1.2 are fixed onto the POE, and this corresponds to a molar mass for the PMM 2.1.2 of 1,150 g/mol.

The thermal analysis of the copolymer reveals a glass transition temperature of −16° C., as well as a melting peak of 45° C. ($\Delta H$=117 J/g).

EXAMPLE 4

Carried out according to the technique described in Example 1, but the ovalbumin (60 mg) is replaced by 2 mg of V3 28 peptide from the V3 BRU loop of the gp 120 of HIV (sequence NNTRKSIHI GPGRAFYATGDIIGDIRQA). The microspheres obtained have an average size of 5.8 microns and 70% of the V3 28 peptide used is encapsulated in the microspheres and this corresponds to an encapsulation of 0.48% w/w. The study made in sweeping electronic microscopy reveals particles which are smooth and spherical.

EXAMPLE 5

Carried out following Example 4 but Pluronic F 68 is added into the aqueous phase containing the peptide at a concentration of 2%. The microspheres obtained have a size of 7.0 microns and 70% of the V3 28 peptide used is encapsulated in the microspheres.

EXAMPLE 6

Carried out following Example 4 but 20 mg of POE-PMM copolymer are added into the aqueous phase containing the peptide.

EXAMPLE 7

Carried out following Example 4 but 20 mg of POE-PMM copolymer are added into the organic phase containing the polymer.

EXAMPLE 8

Carried out following Example 1 but the internal aqueous phase is constituted of 1 ml of 0.5M acetic acid containing 3 mg of type II collagen. The microspheres thus obtained have an average diameter of 6 microns and 66.6% of the collagen used in the preparation is encapsulated in the microspheres of PMM2.1.2, and this corresponds to an encapsulation of 0.7% (w/w).

EXAMPLE 9

Carried out following Example 1 but the internal aqueous phase is constituted of 1 ml of distilled water. The microspheres thus obtained do not contain any biologically active substance. Their average diameter is 7.0 microns.

EXAMPLE 10

Carried out following the technique described in Example 1 but the ovalbumin (60 mg) is replaced by the plasmid pCDNA3 (5 mg).

The microspheres obtained have an average size of 7 μm and 9.8% of the plasmid used is encapsulated in the microspheres and this corresponds to an encapsulation of 0.17% (w/w).

The study made in sweeping electron microscopy reveals particles which are smooth and spherical.

EXAMPLE 11

Carried out following Example 10 but Pluronic® is added into the aqueous phase containing the plasmid, at a concentration of 2%.

The microspheres thus obtained have an average diameter of 7 μm and 12% of the plasmid used is encapsulated in the microspheres and this corresponds to an encapsulation of 0.22% (w/w).

EXAMPLE 12

Carried out following the technique described in Example 1 but the ovalbumin (60 mg) is replaced by the oligonucleotide (pdT16) (2 mg).

The microspheres obtained have an average size of 4.8 μm and 20.6% of oligonucleotide used is encapsulated in the microspheres which represents an encapsulation of 0.19% (w/w).

EXAMPLE 13

Carried out following Example 12 but Pluronico at a concentration of 2% is added into the aqueous phase containing the oligonucleotide.

The microspheres obtained have an average diameter of 5.7 μm and 23% of oligonucleotide used is encapsulated in the microspheres which corresponds to an encapsulation of 0.21% (w/w).

What is claimed is:

1. microspheres having an average diameter of between 1 μm and 100μm comprising a continuous network of a support material, said network being selected from the group consisting of a dense network and a network incorporating a dispersed aqueous phase, said support material containing at least 70% by weight of a homopolymer comprising recurring units of a general formula (I):

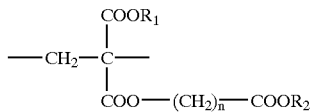

in which:

$R_1$ represents a radical selected from the group consisting of an alkyl group having 1 to 6 carbon atoms and a $(CH_2)_m$ —COOR group in which m is an integer of between 1 and 5 and $R_3$ represents an alkyl group having 1 to 6 carbon atoms;

$R_2$ represents an alkyl group having 1 to 6 carbon atoms; and n is an integer of between 1 and 5;

said homopolymer having a molecular weight of 1,000 to 100,000.

2. Microspheres according to claim 1, wherein the homopolymer comprises recurring units of the general formula (I) in which:

$R_1$ represents an alkyl group having 1 to 6 carbon atoms;

$R_2$ represents an alkyl group having 1 to 6 carbon atoms; and n is 1.

3. Microspheres according to claim 2, wherein the homopolymer comprises recurring units Of the general formula (I) in which R, and $R_2$ represent a $CH_2$—$CH_3$ group.

4. Microspheres according to claim 1, wherein said support material contains:

from 90% to 99.5% by weight of a said homopolymer; and from 0.5% to 10% by weight of a copolymer comprising at least one sequence having a hydrophilic character and at least one sequence having a hydrophobic character, said sequence having hydrophobic character comprising at least one recurring unit of the general formula (I).

5. Microspheres according to claim 4, wherein the sequence having hydrophilic character of said copolymer is selected from the group consisting of a poly(oxyethylene), a poly(vinyl alcohol), a poly(vinylpyrrolidone), a poly(N-2-hydroxypropyl methacrylamide), a poly(hydroxyethyl methacrylate), a hydrophilic poly(amino acid), and a polysaccharide.

6. Microspheres according to claim 4, wherein said copolymer has structure selected from the group consisting of a block structure, a di-block structure, a tri-block structure, and a grafted structure.

7. Pharmaceutical compositions intended for an administration via an oral route, which contain microspheres as defined in claim 1.

8. Microspheres according to claim 1, wherein the homopolymer has a molecular weight of 5,000 to 80,000.

9. Microspheres according to claim 3, wherein the homopolymer has a molecular weight of 5,000 to 80,000.

10. Microspheres having an average diameter of between 1 μm and 100 μm comprising a continuous network of a supports material, in which a substance is dispersed, said network being selected from the group consisting of a dense network and a network incorporating a dispersed aqueous phase, said support material contains at least 70% by weight of a homopolymer comprising recurring units of a general formula (I):

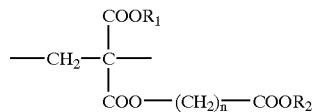

in which:

$R_1$ represents a radical selected from the group consisting of an alkyl group having 1 to 6 carbon atoms and a $(CH_2)_m$ —$COOR_3$ group in which m is an integer of between 1 and 5 and $R_3$ represents an alkyl group having 1 to 6 carbon atoms;

ad $R_2$ represents an alkyl group having 1 to 6 carbon atoms; and n is an integer of between 1 and 5;

said homopolymer having a molecular weight of 1,000 to 100,000.

11. Microspheres according to claim 10, wherein the homopolymer comprises recurring units of the general formula (I) in which:

$R_1$ represents an alkyl group having 1 to 6 carbon atoms;

$R_2$ represents an alkyl group having 1 to 6 carbon atoms; and n is 1.

12. Microspheres according to claim 11, wherein the homopolymer comprises recurring units of the general formula (I) in which $R_1$ and $R_2$ represent a $CH_2$–$CH_3$ group.

13. Microspheres according to claim 10, wherein said support material contains:

from 90% to 99.5% by weight of said homopolymer; and from 0.5% to 10% by weight of a copolymer comprising at least one sequence having a hydrophilic character and at least one sequence having a hydrophobic character, said sequence having hydrophobic character comprising at least one recurring unit of the general formula (I).

14. Microspheres according to claim 13, wherein the sequence hydrophilic character of said copolymer is selected from the group consisting of a poly(oxyethylene), a poly(vinyl alcohol), a poly(vinylpyrrolidone), a poly(N-2-hydroxypropyl methacrylamide), a poly(hydroxyethyl methacrylate), a hydrophilic poly(amino acid), and a polysaccharide.

15. Microspheres according to claim 13, wherein said copolymer has c structure selected from the group consisting of a block structure, a di-block structure, a tri-block structure, and a grafted structure.

16. Microspheres according to claim 10, wherein said substance is a biologically active substance.

17. Microspheres according to claim 16, wherein said dispersed substance is a peptide.

18. Microspheres according to claim 16, wherein said dispersed substance is a protein.

19. Pharmaceutical compositions intended for an administration via an oral route, which contain microspheres as defined in claim 10.

20. Microspheres according to claim 10, wherein the homopolymer has a molecular weight of 5,000 to 80,000.

21. Microspheres according to claim 12, wherein the homopolymer has a molecular weight of 5,000 to 80,000.

22. A method of preparing microspheres having an average diameter of between 1µm and 100 µm, constituted of a continuous network of a support material, said network incorporating a dispersed aqueous phase; said support material containing at least 70% by weight of a homopolymer constituted of recurring units of the following general formula (I):

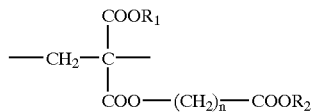

in which:
R$_1$ represents a radical selected from the group consisting of an alkyl group having 1 to 6 carbon atoms and a (CH$_2$)$_m$ —COOR$_3$ group in which m is an integer of between 1 and 5 and R$_3$ represents an alkyl group having 1 to 6 carbon atoms;

R$_2$ represents an alkyl group having 1 to 6 carbon atoms; and n is an integer of between 1 and 5;

said homopolymer having a molecular weight of 1,000 to 100,000, comprising the steps of:
a) preparing a first solution of the polymer comprising the support material in a volatile organic solvent;
b) preparing a second solution non-miscible with the solution obtained in step a);
c) preparing a first emulsion by dispersing the second solution in the first solution, the solution of polymer forming a continuous phase;
d) preparing a second emulsion either by dispersing, with agitation, the first emulsion obtained in step c) in a dispersing medium non-miscible with said first emulsion, or by pouring with agitation, into said first emulsion, a solution comprising a medium non-miscible with said first emulsion; and
e) evaporating said organic solvent with agitation.

23. The method according to claim 22, which further comprises a step e') of displacement of said organic solvent, said step e') being carried out between step d) and step e).

24. The method according to claim 22, which further comprises the steps of:
f) isolating the microspheres by centrifugation;
g) one or more successive washings of said microspheres; and
h) lyophilizing said microspheres.

25. The method according to claims 23, which further comprises the steps of:

f) isolating the microspheres by centrifugation;
g) one or more successive washings of said microspheres; and
h) lyophilizing said microspheres.

26. A method of preparing microspheres having an average diameter of between 1µm and 100µm, constituted of a continues network of a support material, said network incorporating a dispersed aqueous phase; said support material containing at least 70% by weight of a homopolymer constituted of recurring units of the following general formula (I):

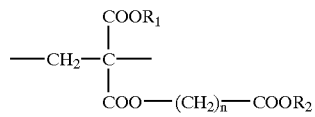

in which:
R$_1$ represents a radical selected from the group consisting of an alkyl group having 1 to 6 carbon atoms and a (CH$_2$)$_m$ —COQR$_3$ group in which is an integer of between 1 and 5 and R$_3$ represents an alkyl group having 1 to 6 carbon atoms;

R$_2$ represents an alkyl group having 1 to 6 carbon atoms; and n is an integer of between 1 and 5;

said homopolymer having a molecular weight of 1,000 to 100,000, comprising the steps of:
a) preparing a first solution of the polymer comprising the support material in a volatile organic solvent;
b) preparing a second solution non-miscible with the solution obtained in step a), containing said substance to be dispersed;
c) preparing a first emulsion by dispersing the second solution in the first solution, the solution of polymer forming a continuous phase;
d) preparing a second emulsion either by dispersing, with agitation, the first emulsion obtained in step c) in a dispersing medium non-miscible with said first emulsion, or by pouring with agitation, into said first emulsion, a solution comprising a medium non-miscible with said first emulsion; and
e) evaporating said organic solvent with agitation.

27. The method according to claim 26, which further comprises a step e') of displacement of said organic solvent, said step e') being carried out between step d) and step e).

28. The method according to claim 26, which further comprises the steps of:
f) isolating the microspheres by centrifugation;
g) one or more successive washings of said microspheres; and
h) lyophilizing said microspheres.

29. The method according to claim 27, which further comprises the steps of:
f) isolating the microspheres by centrifugation;
g) one or more successive washings of said microspheres; and
h) lyophilizing said microspheres.

30. A method of preparing microspheres having an average diameter of between 1µm and 100µm, constituted of a continuous network of a support material, said network incorporating a dispersed aqueous phase; said support material containing at least 70% by weight of a homopolymer constituted of recurring units of the following general formula (I):

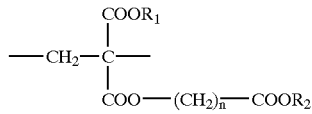

in which:
R$_1$ represents a radical selected from the group consisting of an alkyl group having 1 to 6 carbon atoms and a (CH$_2$)$_m$ —COOR$_3$ group in which m is an integer of between 1 and 5 and R$_3$ represents an alkyl group having 1 to 6 carbon atoms;
R$_2$ represents an alkyl group having 1 to 6 carbon atoms; and
n is an integer of between 1 and 5;
said homopolymer having a molecular weight of 1,000 to 100,000,
comprising the steps of:
 a) preparing a first solution of the polymer mentioned above comprising the support material in a volatile organic solvent, containing a surfactant agent;
 b) preparing a second solution non-miscible with the solution obtained in step a), and a surfactant agent;
 c) preparing a first emulsion by dispersing the second solution in the first solution, the solution of polymer forming a continuous phase;
 d) preparing a second emulsion either by dispersing, with agitation, the first-emulsion obtained in step c) in a dispersing medium non-miscible with said first emulsion, said dispersing medium containing a stabilizing agent, or by pouring with agitation, into said first emulsion, a solution comprising a medium non-miscible with said first emulsion, said medium containing a stabilizing agent; and
 e) evaporating said organic solvent with agitation.

31. The method according to claim 30 wherein the surfactant agent used for preparing the first emulsion is selected from the group consisting of poloxamers, polysorbates, poly(vinyl alcohols) and copolymers comprising at least one sequence having a hydrophilic character and at least one sequence having a hydrophobic character, said sequence having hydrophobic character comprising at least one recurring unit of the general formula (I).

32. The method according to claim 30, wherein said stabilizing agent used for preparing the second emulsion is a poly(vinyl alcohol).

33. A method of preparing microspheres having an average diameter of between 1 μm and 100 μm, constituted of a continuous network of a support material, said network incorporating a dispersed aqueous phase; said support material containing at least 70% by weight of a homopolymer constituted of recurring units of the following general formula (I):

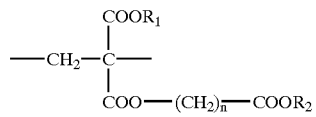

in which:
R$_1$ represents a radical selected from the group consisting of an alkyl group having 1 to 6 carbon atoms and a (CH$_2$)$_m$ —COOR$_3$ group in which m is an integer of between 1 and 5 and R$_3$ represents an alkyl group having 1 to 6 carbon atoms;
R$_2$ represents an alkyl group having 1 to 6 carbon atoms; and
n is an integer of between 1 and 5;
said homopolymer having a molecular weight of 1,000 to 100,000,
comprising the steps of:
 a) preparing a first solution of the polymer comprising the support material in a volatile organic solvent, containing a surfactant agent;
 b) preparing a second solution non-miscible with the solution obtained in a), containing said substance to be dispersed, and a surfactant agent;
 c) preparing a first emulsion by dispersing the second solution in the first solution, the solution of polymer forming a continuous phase;
 d) preparing a second emulsion either by dispersing, with agitation, the first emulsion obtained in c) in a dispersing medium non-miscible with said first emulsion, said dispersing medium containing a stabilizing agent, or by pouring with agitation, into said first emulsion, a solution comprising a medium non-miscible with said first emulsion, said medium containing a stabilizing agent; and
 e) evaporating said organic solvent with agitation.

34. The method according to claim 33, wherein the surfactant agent used for preparing the first emulsion is selected from the group consisting of poloxamers, polysorbates, poly(vinyl alcohols) and copolymers comprising at least one sequence having a hydrophilic character and at least one sequence having a hydrophobic character, said sequence having hydrophobic character comprising at least one recurring unit of the general formula (I).

35. The method according to claim 33, wherein said stabilizing agent used for preparing the second emulsion is a poly(vinyl alcohol).

* * * * *